ced by examiner

United States Patent
Raghavan et al.

(10) Patent No.: US 9,757,543 B2
(45) Date of Patent: Sep. 12, 2017

(54) DELIVERY OF MATERIALS INTO MARGINS OF TISSUE CAVITIES

(71) Applicants: Raghu Raghavan, Baltimore, MD (US); Martin Brady, Monkton, MD (US)

(72) Inventors: Raghu Raghavan, Baltimore, MD (US); Martin Brady, Monkton, MD (US)

(*) Notice: Subject to any disclaimer, the term of this patent is extended or adjusted under 35 U.S.C. 154(b) by 753 days.

(21) Appl. No.: 14/229,876

(22) Filed: Mar. 29, 2014

(65) Prior Publication Data

US 2014/0303593 A1   Oct. 9, 2014

Related U.S. Application Data

(60) Provisional application No. 61/807,859, filed on Apr. 3, 2013.

(51) Int. Cl.
*A61M 31/00* (2006.01)
*A61M 37/00* (2006.01)
*A61M 25/10* (2013.01)

(52) U.S. Cl.
CPC ....... *A61M 25/10* (2013.01); *A61M 2025/105* (2013.01); *A61M 2025/1086* (2013.01)

(58) Field of Classification Search
CPC ............ A61M 2025/105; A61M 25/10; A61M 2025/1086; A61M 2025/1013
USPC ..................................................... 604/103.01
See application file for complete search history.

(56) References Cited

U.S. PATENT DOCUMENTS

2009/0254064 A1* 10/2009 Boatman ............ A61M 25/1011
604/509

* cited by examiner

*Primary Examiner* — Jason Flick
(74) *Attorney, Agent, or Firm* — Mark A. Litman; Mark A. Litman & Associates, P.A.

(57) ABSTRACT

Surgery is performed on a patient with a novel device by:
excising tissue from tissue mass within a patient to create a cavity within the tissue mass;
inserting a novel device of this invention into the cavity;
shaping a flexible expandable component of the device to adjust dimensions on the flexible expandable component;
providing a liquid into the component through the liquid input port; and
controlling pressure or flow rate of the liquid in the component to move the liquid through the multiple openings and into the cavity.

The device has a liquid inlet port, an exterior surface having length, width and depth, and multiple openings in the surface distributed throughout the length, width and depth to act as liquid delivery ports;
the exterior surface of the liquid delivery device being shapeable by internal pneumatic pressure or hydraulic pressure to better fit inside dimensions of a surgical cavity;
the multiple openings deliver the liquid through the multiple openings.

20 Claims, 8 Drawing Sheets

Figure 8:

CMID

DELIVERY OF MATERIALS INTO MARGINS OF TISSUE CAVITIES

RELATED APPLICATION DATA

This application claims priority from U.S. Provisional Patent Application Ser. No. 61/807,859, filed 3 Apr. 2013.

BACKGROUND OF THE INVENTION

1. Field of the Invention

The present invention relates to the field of medical technology, delivery of materials in the field of medical technology, and the controlled and directed delivery of materials to regions of tissue in the vicinity of cavities.

2. Background of the Art

After tissue has been removed by surgical techniques of various types, cavities remain in remaining tissue in the region of the surgery. The remaining tissue may be subject to various complications after the surgery has been completed. For example, resection margin cavity recurrence after surgical removal of glioblastoma occurs in more than 80% of patients, despite extensive trials of local and generalized treatment regimens. While it is likely that some tumor cells have migrated through white matter tracts to more distal portions of the brain by the time of initial diagnosis, the persistence of tumor cells within the cavity margin eventually creates a local tumor recurrence and also serves as a continuing source for metastasis. Whereas the surgically resected tumor has essentially all cells malignant, the margins of the tumor may be infiltrated with tumor cells in a ratio of 1:10 or so. Therefore, effective post-surgical treatment of the cavity margin will both reduce the morbidity and cost of treating a local recurrence and remove a prominent source of cells for ongoing metastasis to other parts of the brain. It is not realistic to assure the absence of small numbers of tumor cells in such adjacent tissue through extensive removal of tissue, as this would require excessive normal tissue damage. Especially in regions of the brain, extreme excavation of tissue is not a desirable medical procedure.

One relatively standard treatment at this time is that, after surgery has been performed and some recovery period (days or weeks) has been allowed to transpire, a second surgical procedure is performed wherein the region around the cavity is recatheterized. Active material is then infused and diffused about the cavity (into tissue outside the cavity) to chemically attack (preferentially) remaining tumor cells. This type of procedure has a number of defects and disadvantages. A second surgical procedure, with possibly a second distinct bore-hole is required, and the present methods of active ingredient delivery in this procedure tend to be inefficient and inexact.

Among the methods that have been used to treat this problem include: (i) Radiation therapy followed by systemic chemotherapy. The distribution of chemotherapeutic materials administered systemically is highly dependent on the state of the opening of the blood—brain barrier (BBB) and little significant concentration is expected in uncompromised BBB regions; (ii) Placement of wafers containing chemotherapeutics at margin walls. This has the advantage that it can be done at the time of surgery in the operating theater. Its disadvantage is that the chemotherapy spreads by diffusion: the slow rate of diffusive spread combined with high efflux rates of small molecules means the spread is confined to a millimeters instead of centimeters. Despite the FDA approval of this method, it has only marginally improved the survival rate of patients.

Additional alternative methods include (iii) Multicatheter convection—enhanced delivery (CED) from up to four catheters. This is the method that has been most used in clinical trials with CED, and the usual advantage mentioned is the potentially superior spread of infusate from CED over diffusion of the agent. Its principal disadvantage is that it requires a second invasive operation, more so due to the multiple catheters required. Moreover, it is immediately obvious that coverage of a 2 cm margin (which is a thick shell from discrete point or line sources) will require an unacceptable number of catheters, so that CED may fail to cover such a margin. Indeed this has been pointed out as a potential reason for failure of a trial. (iv) It has been advocated that an inside—out approach may be the best modality. Namely, if the infusion occurs from within the cavity, we have, in principle, the entire inner surface of the margin as a source of infusion which should then fill the shell far more uniformly than any of the approaches above.

SUMMARY OF THE INVENTION

Upon surgical creation of a cavity, active ingredients to treat cells and tissue surrounding the cavity are introduced from a delivery element having a highly dispersive delivery function from its surface, forming a marginal area around the cavity. The present technology provides a delivery system having a significant portion of a delivery surface allowing diffuse delivery of actives from significant numbers of different areas, or volumes over numerous areas or different components across the surfaces of the delivery surface. The openings on the delivery surface should have reduced or minimal variation in size as a function of pressure from the internally delivered liquid active materials. The resistance of these openings to fluid flow should likely dominate other resistances to fluid flow so that the delivery proceeds approximately uniformly from all the openings into the tissue. This technology is referred to herein as cavity margin infusion devices (CMID).

DETAILED DESCRIPTION OF THE INVENTION

Figure 1:
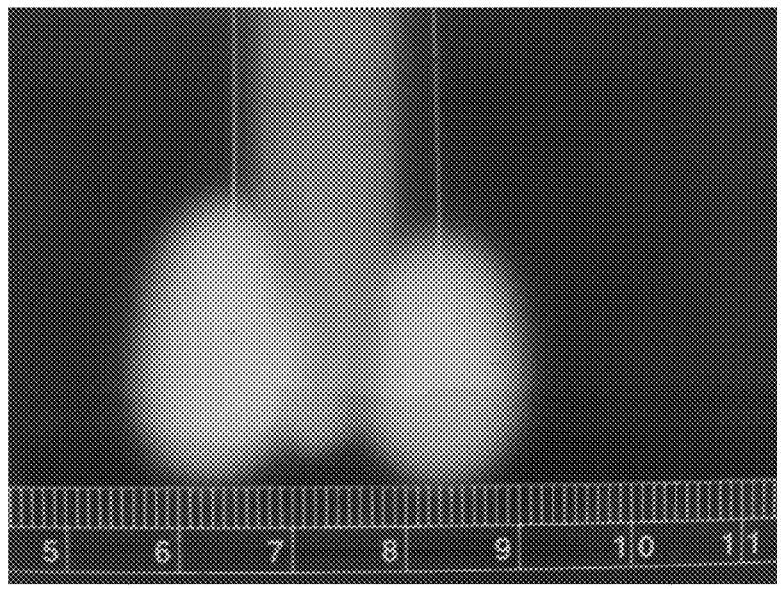
FIG. 1. (Prior art) Multiple catheters in the margin. Chief defect: the shapes of the infusion do not necessarily conform to the shape of the margin, which is a thick shell surrounding the cavity. This requires too many catheters to fill the margin, which is surgically unacceptable. Other problems: The procedure is limited in flow rates since backflow may be unacceptably large and take the infusion out of the brain into the sub-arachnoid spaces containing CSF, and consequent lose a lot of the infusate. A third disadvantage (also illustrated) is that as the infusate reaches the cavity it will readily continue to flow into and fill the cavity, where the infusate does not perform any useful function (there is no cancer there for the therapy to act upon). In all illustrations, the darker shade illustrates the color density of bromophenol blue dye used in the infusion procedure.

There are numerous structures and methodologies within the generic scope of the present technology, cavity margin infusion devices (CMID). As mentioned before, the present technology advocates that an inside-out approach may be the best format for delivery of active liquid materials after excavation or incision to form a cavity within tissue mass. Namely, if the infusion occurs from within the cavity, we have, in principle, the entire inner surface of the margin as a source of infusion which should then fill a region of tissue surrounding the cavity (i.e. the margins of the cavity) far more uniformly than any of the prior art approaches discussed above. Our approach is a specific realization of this strategy: what is described in the present inventive CMID and methods includes an intracavitary balloon (see Olson J J, Zhang Z, Dillehay D, Stubbs J. Assessment of a balloon-tipped catheter which has been designed as described herein for intracerebral convection-enhanced delivery. *J Neurooncol*. September 2008; 89(2):159-168 after the cavity has been resealed. Both of these require a separate surgical intervention some weeks after the resection. Since we will compare our device with the approaches in (iii) and (iv) in detail below, we shall defer further discussion on these methods below.

It is to be noted that the term "balloon" refers to an inflatable device, but not necessarily a component in which the surface structure significantly elongates. Balloon is a convenient term, as the component may inflate from a collapsed state, but it may or may not have the material forming the surface of the balloon significantly stretch or elongate. For example, in an outer balloon, in a two balloon composite component, limited (e.g., less than 10%, less than 8%, less than 5%, and even less than 2% elongation during maximum pneumatic pressure (gaseous) or hydraulic (fluid, including liquid) pressure applied into the internal volume of the balloon) may be desirable, as the reduced or non-existent elongation will maintain opening sizes in the surface of the balloon at a predetermined size. Lack of elongation will assist in enabling that these opening sizes do not vary and that release of liquid from the balloon will remain relatively constant at given liquid pressure levels. Also as previously noted, the resistance of these openings to fluid flow should likely dominate other resistances to fluid flow so that the delivery proceeds uniformly from all the openings into the tissue. This means that the openings or liquid ports may be either high resistance or low resistance. As the pressure should not alter the size of the ports significantly (as elsewhere explained), a rate of delivery will be dependent upon the internal pressure on the fluid, and should remain constant at constant pressure with a given port dimension, no matter what the resistance of the ports. Balloon materials, and other expandable or flexible elements as used in the present disclosure includes elastomers and rubbers, both natural and synthetic such as silicone rubbers or elastomers, urethane elastomers, ethylenic elastomers (such as those made from butadiene, polystyrene, acrylic materials, and the like), fluoro-elastomers, and other flexible materials.

The present technology can be generally described as including a method of providing medically active liquid to tissue (especially the surface of tissue) surrounding a surgically-created cavity. The method may include: a) positioning a liquid-delivery device within the cavity; b) the delivery device having an exterior surface, length, width and depth, and multiple openings in the exterior surface distributed throughout the length and width of the delivery device; c) adjusting dimensions of the exterior surface of the liquid delivery device to better fill inside dimensions of the cavity; d) delivering the medically active liquid to the tissue surrounding the surgically-created cavity through the multiple openings; and e) moving the medically active liquid out of the multiple openings at a delivery rate through the multiple openings. The method may be performed where the medically active liquid is moved out of the multiple openings at a delivery rate through the multiple openings such that a delivery rate through a single one of the multiple openings does not vary by more than 20% in micrograms/liter from a numerical rate average for all of the multiple openings. The delivery device may be, for example, a flexible and inflatable component having a surface and a volume, with the multiple openings distributed in three dimensions over the surface of the inflatable component. The multiple openings distributed in three dimensions over the surface of the volume may be provided by at least four liquid-delivery catheters distributed over the surface of the inflatable component, each liquid delivery catheter having multiple ones of the multiple openings along lengths of the liquid delivery catheters, and the medically active liquid is delivered from the liquid delivery catheters through the multiple ones of the multiple openings along lengths of the liquid delivery catheters. The multiple openings distributed in three dimensions over the surface of the volume may alternatively be at least sixteen liquid-delivery catheters distributed over the surface of the inflatable component, each liquid delivery catheter comprising a narrow tube with a distal opening, or an end port catheter. These catheters may be of being of different lengths so that the at least 16 openings are distributed over the surface of the inflatable component, and the medically active liquid is delivered from the liquid delivery catheters through the multiple openings at the ends of the liquid delivery catheters. The inflatable component may be shaped (inflated to its natural shape or in conformation with at least some of the tissue surface within the cavity, at its margins) by application of pneumatic pressure or hydraulic pressure within the inflatable component to conform the surface of the inflatable element to interior walls of the cavity. It is hereby noted that the cavity walls can be deformed to conform to the shape of a balloon as well, within limits of the extent of the deformation The inflatable component may alternatively be an inner flexible balloon and an outer flexible balloon, the outer flexible balloon having the multiple openings therein, the method further comprising providing the medically active liquid into a volume between the inner flexible balloon and the outer flexible balloon. The pneumatic pressure or hydraulic pressure may be imposed in the balloon or on the medically active liquid within the volume between the inner flexible balloon and the outer flexible balloon, forcing the medically active liquid to pass through the multiple openings in the outer flexible balloon. The medically active liquid may be delivered into each liquid delivery catheter at equal pressure or delivered into each liquid delivery catheter at an individually controlled pressure for each liquid delivery catheter. This may be done by a processor controlling individual pressures at valves, restrictors, solenoids and other fluid and/or pressure control systems.

One additional alternative for providing a distributed network of release ports over the surface of the balloon would be as sources of fluid being distributed over the surface of cavity wall/balloon as nubs, points, elevated structures, indentations, islands, pyramidal structures and the like, forming a "porcupine" approach to distribution of the delivery ports. The raised or indented structures would have pores or openings therein, as with the other described structures in this invention. The balloon surface may be studded with small needles or short catheters directed transverse to the surface (for example, perpendicular, but any angle not parallel tangential to the surface may be an embodiment of this alternative. The tangential or parallel case is already taken care of by other descriptions of technology provided herein in the practice of our invention]. These porcupine structures may even slightly penetrate the tissue. This is also a realization of the distributed sources.

The multiple openings distributed in three dimensions over the surface of the volume may be at least eight flexible liquid delivery catheters distributed over the surface of the inflatable component, each liquid delivery catheter having multiple ones of the multiple openings along lengths of the liquid delivery catheters, and the medically active liquid is delivered from the liquid delivery catheters through the multiple ones of the multiple openings along lengths of the liquid delivery catheters. The medically active liquid may be delivered into each liquid delivery catheter at an individually controlled pressure for each liquid delivery catheter.

The generic liquid-delivery devices used within the practice of the present technology may have a liquid inlet port, an exterior surface having length, width and depth, and multiple openings in the surface distributed throughout the length and width and/or depth to act as liquid delivery ports; dimensions of the exterior surface of the liquid delivery device being shapeable by internal pneumatic pressure or hydraulic pressure to better fill, or locate or conform to inside dimensions of a surgical cavity; the multiple openings are sized to deliver the liquid at delivery rates through the multiple openings.

The multiple openings may be configured such that a delivery rate through a single one of the multiple openings does not vary by more than 20% or more than 15% or more than 10% in micrograms/liter from a numerical rate average for all of the multiple openings.

The multiple openings may be multiple openings distributed along lengths of at least four flexible liquid delivery catheters distributed over an outer surface of a flexible expandable component having a pneumatic pressure inlet or hydraulic pressure inlet carrier engaged to an interior of the flexible expandable component, or the multiple openings comprise multiple openings distributed along lengths of at least eight flexible liquid delivery catheters, preferably symmetrically distributed over an outer surface of a flexible expandable component having a pneumatic pressure inlet or hydraulic pressure inlet carrier engaged to an interior of the flexible expandable component to enable the liquid delivery device to be shapeable.

The multiple openings may be provided as multiple openings distributed along a surface of a first flexible inflatable balloon, the first flexible balloon defining an internal volume, the internal volume containing a second flexible inflatable balloon. The liquid input port may be in liquid delivery communication with a liquid support volume between the first flexible inflatable balloon and the second flexible inflatable balloon. At least one of the flexible liquid-delivery catheters is moveable along the outer surface of the flexible component so that the at least one flexible liquid-delivery catheter can be moved further from one adjacent catheter and closer to another adjacent catheter.

A method of performing surgery on a patient may include steps of:
- excising tissue from tissue mass within a patient to create a cavity within the tissue mass;
- inserting the (CMID) devices described herein into the cavity;
- shaping the flexible expandable component with pneumatic pressure or hydraulic pressure to adjust dimensions on the flexible expandable component within an interior contour of the cavity;
- providing a liquid into the component through the liquid input port; and
- controlling pressure on the liquid in the expandable component to move the liquid through the multiple openings and into the cavity.

The liquid moved through the openings may be supported on exterior surfaces such as a porous film of the expandable component against internal tissue surfaces in the cavity. The liquid may be preferably moved through the openings and into the cavity within 2 hours, within 90 minutes, within 60 minutes, within 45 minutes, within 30 minutes, within 15 minutes within 10 minutes, within 5 minutes or within 2 minutes of excision of tissue.

Figure 7:
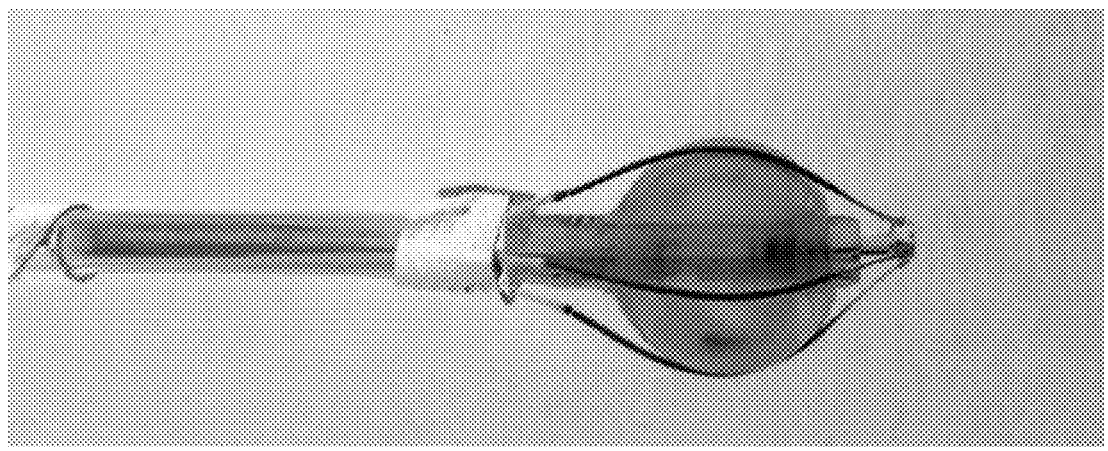
FIG. 7 shows a first embodiment of a balloon delivery catheter within the generic practices of the present invention, a prototype used in preliminary gel tests. The white cords are porous membrane catheters with micropores along its length—four of these were used.
Figure 8:
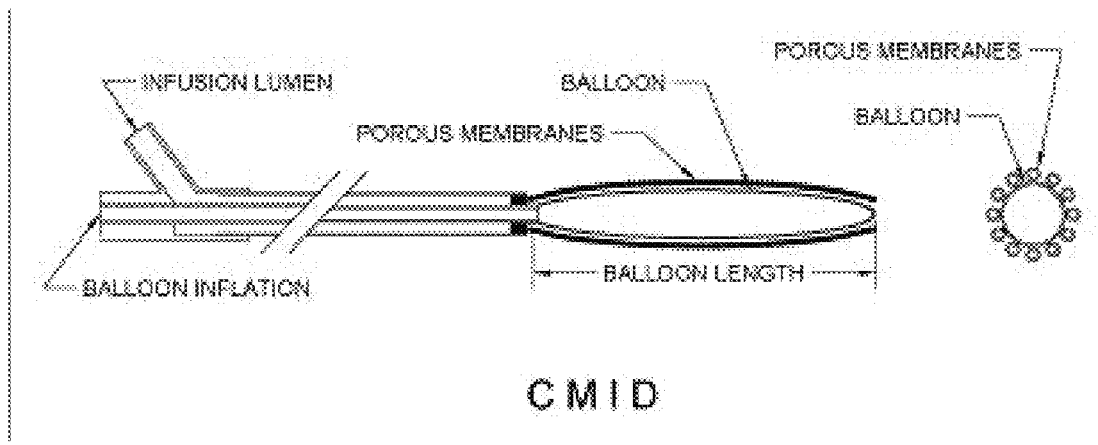
FIG. 8 shows a second embodiment of a balloon delivery catheter within the generic practices of the present invention in twelve (12) porous membrane catheters are distributed along the meridians of the balloon and all feed into a manifold so that a single pump is distributing fluid. This is possible only because the resistance of these catheters is very high so that it will not happen that all the fluid goes through only one catheter. Any small variations in resistance will not have a dramatic effect on the distribution of flow.
Figure 13:
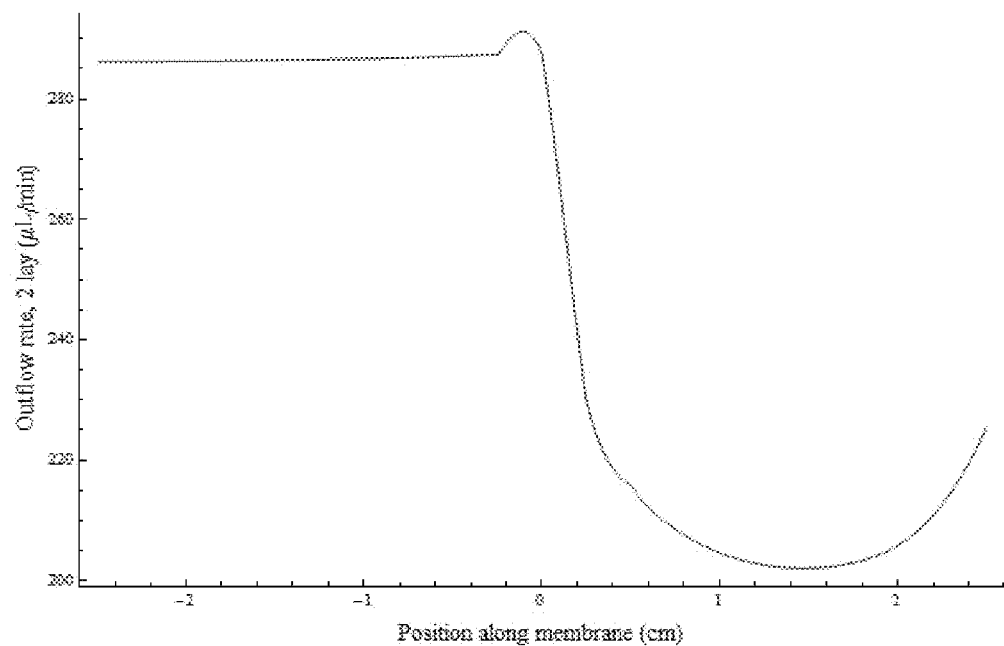
FIG. 13 is a graphic representation that shows the distribution of flow rate per unit length in the case of ports which are impedance matched to tissue.
Figure 14:
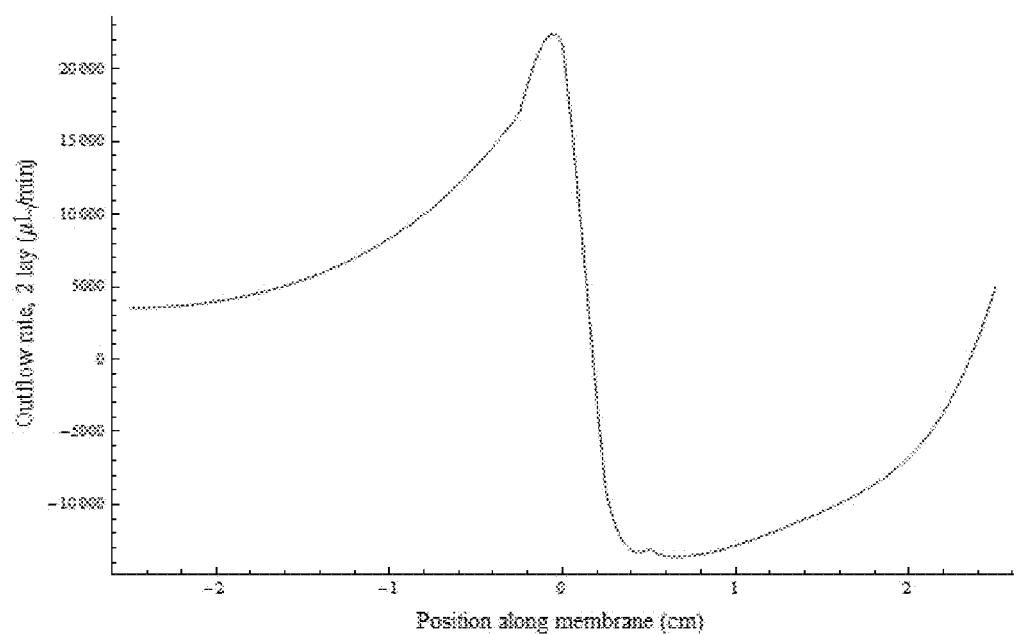
FIG. 14 is a graphic representation that shows the distribution of flow rate over unit length and which shows the results where the only change made from the system of FIG. 13 is that the ports are 30 times more conductive.

The use of wide-field, high-flow volume capability delivery surfaces, such as porous films, porous sheets, surfaces with openings distributed thereon, multiple liquid delivery microcatheters with openings distributed over a surface, or hollow fiber catheters with infusion surfaces, assist in the development of a conforming balloon-based platform upon which multiple effusion openings, a distribution of openings over a surface and the like, including side-hole liquid delivery catheters that may be arrayed in parallel rows on the balloon surface. The side holes may be radially perpendicular with respect to the balloon surface, or may be angled away from perpendicular (but not blocked by the balloon the surface) so that when the catheters are pressed against tissue on the cavity walls, the effusion openings are not blocked. These catheters become firmly pressed to, adjacent to or along the wall of the resection cavity when the balloon is fully inflated within the cavity, or inflated to an extent desired to form an appropriate delivery shape, contour or distribution effect from the balloon and the liquid-delivery openings. See FIGS. 7, 8. Fluid and agent perfuse the entire cavity tissue surface through the millions of pores along the entire length of each catheter, and the infusate (liquid medically active material, which includes solutions, suspensions, emulsions and the like) distributes uniformly through the interstitial spaces of the resection cavity margin tissue. The impedance of the catheter pores and tissue interstitial spaces is sufficiently similar to provide effective fluid and agent transfer, in contrast to the impedance mismatch observed with the typical infusion needle or balloon catheter. The fluid conductivity (which is the inverse of resistivity) of brain tissue for example, be it white matter or gray matter is at least as great as $10^{-9}$ cm$^4$/(dyne-seconds). If however, the port of the catheter faces a fluid space, for example, a ventricular space in brain, then the conductivity it sees is essentially infinity. However, this need not concern us, since we need to design for the lower limit. In other words, the effective resistance of the port must be at least as great as that of the tissue it faces. In order to illustrate the difference this makes, we first discuss FIGS. 13 and 14 shown. These figures illustrate the difference between high and low resistance ports distributed along a line for viewing convenience. A total flow rate of 1.25 milliliters per minute is infused over a length of 5 cm in both cases. FIG. 13 shows the distribution of flow rate per unit length in the case of ports which are impedance matched to tissue, but where half of the length faces tissue (the region of the abscissa from 0 to 2.5 cm) and the second half of the length (from −2.5 cm to zero) faces fluid. A tissue hydraulic conductivity of $10^{-7}$ cm$^4$/(dyne-seconds) was chosen, while that of the fluid, as stated was chosen to be infinite. The ports distributed densely along the length were assumed to have the same conductivity as tissue. It is seen from FIG. 13 that the outflow rate is reasonably uniform. If it were strictly uniform then it would be constant at 250 microliters per minute. As is seen it is somewhat higher than that flowing into the fluid region, and somewhat lower than that flowing into the tissue. However, the tissue is indeed infused with fluid. On the other hand, FIG. 14 shows the results where the only change made is that the ports are 30 times more conductive. The result is substantial failure of acceptable performance. Fluid from tissue is actually sucked into the catheter at a high rate and comes out into the fluid portion. Not only is the tissue not perfused, this is likely to clog the catheter with tissue, with a resulting build-up of pressure, and catastrophic failure, The calculation does not take these possible sequelae into account and merely shows the picture of what would happen if the flow proceeded steadily. With port resistance even higher than that in FIG. 13 (i.e., dominating the fluid resistance), the outflow rate would have been even more uniform. The design principle for the present invention will use such simulations and measurements on tissue to optimize the port resistances and their distribution over the surface area of the inside of the cavity (or outside of the inflatable component such as the balloon).

Moreover, the much wider fluid source area created by the distribution of delivery tubes, which effectively becomes the entire balloon surface, permits significantly greater flow rates of fluid and agent. Cavity margin treatment can be given in the immediate post-resection interval, eliminating a second, later surgery to remove the treatment apparatus as is required for conventional multi-catheter or intracavitary balloon CED.

Figure 6:
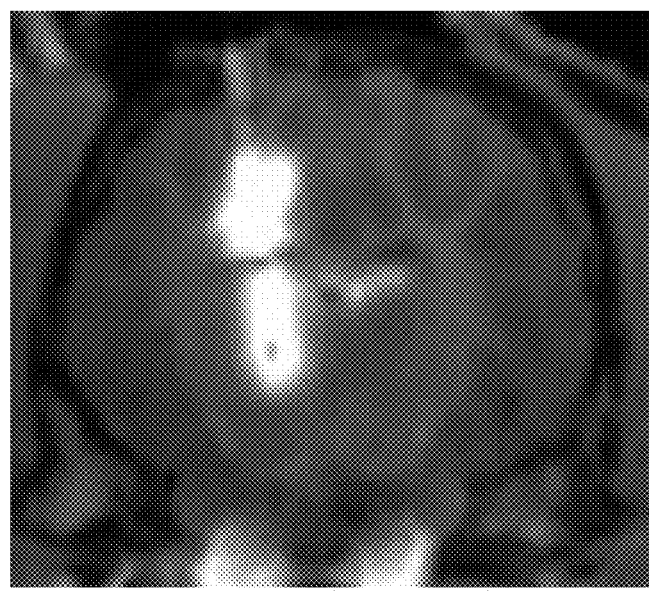
FIG. 6 (bridging sinks)]. This Figure illustrates a porous membrane supporting fluid egress over its entire length due to the multiple microports. In the example shown, there is a ventricle (dark isthmus between the bright infusions highlighted by a MR contrast reagent (Gadolinium) which is a sink for fluid. The infusion successfully fills the tissue both above and below the ventricle. An end-port catheter would be able to cover only from the distal end to the ventricle and not be able to bridge it.

Fluid loss into low-pressure sinks, such as sulci or other tissue breach, is minimized by the bridging ability of the hollow fiber catheter to infuse fluid directly into tissue from the pores along the catheter length on either side of the sink. Effective tissue perfusion is thereby maintained. See FIGS. 3, 6 for a comparison between a conventional balloon catheter and a multi-microport catheter: in the particular case of FIG. 6 this is Twin Star Medical's hollow fiber catheter technology. Such microport technology may be provided, by way of non-limiting examples, with at least some of the liquid-delivery catheters present as a) porous membrane(s) or b) closed tubes with multiple microports drilled, punctured or etched into walls of the tube. The drilling may be done mechanically, by laser drilling, or even by photolithographic etching.

Cavity margin infusion devices (CMID), including the balloon-based structures described herein, further including the herein described and enabled multiple hollow fiber catheter technology delivered with a conformable balloon platform may become standard treatment for glioblastoma patients post-resection. Even with apparently total resection of a tumor, malignant cells remain in the cavity margin in virtually every patient. Patients will not have a complete tumor resection if preservation of eloquent function would be too significantly compromised. For both classes of patients, the specialized catheter assembly provides an innovative treatment, especially for addressing post-surgical resection margin tumor recurrence or persistence.

The focus of tissue CED has largely centered on single end port multi-catheter delivery of fluid, and uneven distribution in tissue has been the norm. The change proposed here is to employ large elution surfaces as the delivery format, including effusion surfaces and hollow fiber technology, on a supporting balloon platform, to perfuse the entire surface of the at-risk tissue margin rather than inserting a type of catheter directly into margin tissue or the cavity to cause perfusion. Optimal catheter arrays and fluid pressure and flow rates needed to achieve uniform tissue distribution in the (exemplary only) 2 cm cavity margin are discussed and enabled. A range of from 0.5 cm to 8 cm, and preferably from 1.0 cm to 5 cm will be used for typical tumor resections.

One embodiments or species within the generic concepts described herein includes using a conforming balloon to support symmetrical or asymmetrical arrayed catheters against, adjacent to or proximal to the cavity wall represents a novel approach to catheter CED (convection enhanced delivery). We enable methods and structures to allow determination and exploitation of optimal numbers and configurations of hollow fiber catheters for each clinical application—cavity size and configuration—so that the best treatment option is created for each patient. We recognize that in some situations a single infusion may be deemed inadequate, and for future development we plan to explore the use of this infusion device in conjunction with a Rickham reservoir or similar reservoir to deliver multiple or chronic infusions.

The approach of this invention provides a very significant improvement for direct infusions of anti-cancer agents into the margin parenchyma. However, for completeness, we review systemic and wafer placement approaches that have been used, and their advantages and drawbacks.

The applicants propose that the specialized catheter assembly will provide an improvement with respect to asymmetric distribution and low infusion rates seen in brain resection cavity margin infusions. Our preliminary work in a phantom tissue model clearly demonstrates the superiority of the specialized catheter assembly in providing uniform dye distribution and enhanced flow rates.

Balloon Catheter inflated within a completely sealed cavity.

Figure 2:
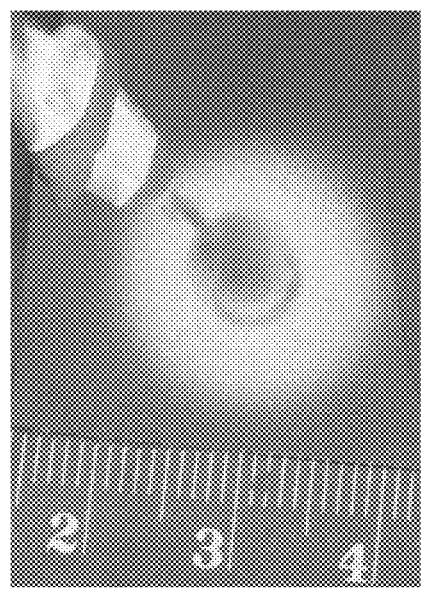
FIG. 2. (Prior art) It has been suggested that inflated balloons be used from within the cavity. When the cavity is completely sealed, such a process will eventually fill the margins as illustrated. The illustration is a photograph that shows that dye moves uniformly into gel from a conventional balloon catheter in a sealed cavity with no pathway such as a pseudosulcus to surface.
Figure 3:
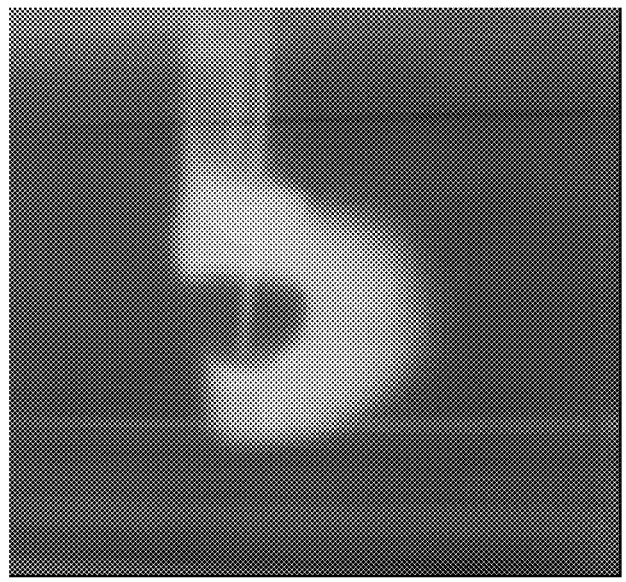
FIG. 3 (Disadvantages of balloon catheter 1) is a photograph of dye leaks into pseudosulcus when a conventional balloon catheter infuses an otherwise completely sealed cavity. The pseudosulcus was created as a slit in the gel. The low resistance pathway via the pseudosulcus completely compromises infusions into the gel body (margins of cavity).
Figure 4:
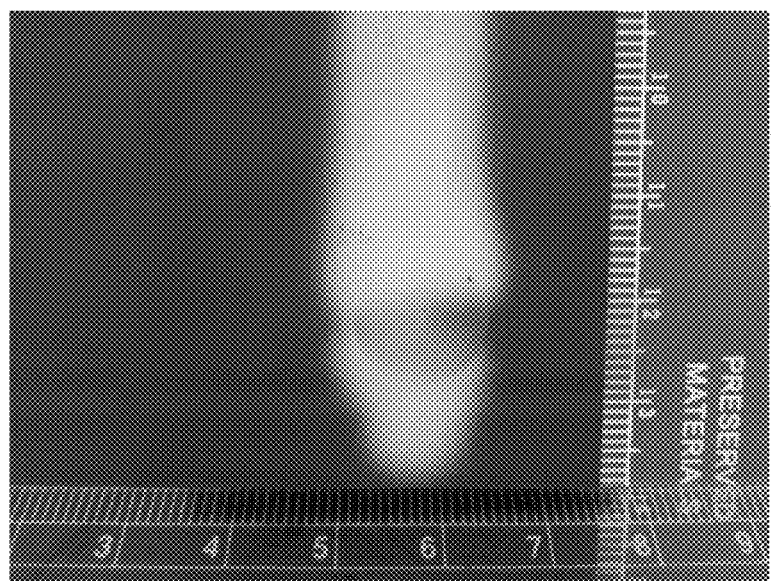
FIG. 4 (Disadvantages of balloon catheter 2) is an image showing that when the cavity is unsealed, as it would be upon tumor resection, the balloon fails to infuse the margins as illustrated. The balloon itself does not offer effective sealing for the fluid from the end port, even with a glue (DuraSeal™ glue) used in neurosurgery. The fluid flows back along the balloon surface and leaks to the top of the gel (corresponding to "the CSF" (cortico spinal fluid) in analogy to brain).

Using a 0.2% agarose tissue phantom gel model, we infused bromophenol blue through the tip of a balloon catheter inflated in a sealed gel cavity. When the balloon was inflated, we observed efficient dispersion of dye into the cavity margin. See FIG. 2. This result may be expected. However, if we either (i) Create a lateral pseudo-sulcus in gel, or (ii) have an unsealed cavity, the balloon catheter completely fails to infuse the margins. These results are illustrated in FIGS. 3 and 4 respectively, and show that the conventional balloon catheter is also not suitable for infusing the margins, albeit for different reasons from that of the use of multiple catheters within the tissue margin. The CMID addresses defects in both these approaches, and allows an advantage of intracavitary infusions to become effective despite the presence of sulci or the unsealed nature of the cavity which exists immediately after surgery in the operating theater. The CMID is the only technology, amongst those addressed here and that we are aware of, that may be applied under these conditions as an extension of the resection surgical procedure within the operating theater to infuse therapeutics into the margins of the cavity. We also recognize that in some situations a single infusion may be deemed inadequate, and the CMID may in such circumstances be used in conjunction with a Rickham reservoir or similar reservoir to deliver multiple or chronic infusions. Therefore, even though one preferred embodiment of the present technology is immediate infusion after resection surgery, the novel devices of the present invention may be used in later surgical administrations of infusate.

Multiple Catheters to infuse cavity margin.

Multicatheter convection—enhanced delivery (CED) using as many as four catheters is the method most used in CED clinical trials to infuse tumor-infiltrated tissue in the margins of a cavity after tumor resection, and the advantage cited is its potentially superior distribution of infusate compared with diffusion of the agent. A major disadvantage in CED usage is that a subsequent (to resection) procedure is required to place and to remove the multiple catheters. More importantly, uniformly infusing an exemplary 2 cm margin from discrete point sources would require an unacceptable number of catheters. FIG. 1 shows a pattern of spread (of dye in gel) that illustrates that covering the margins will require a very large number of catheters: further a three-dimensional cavity which is roughly ellipsoidal will demand unacceptable multiple catheter trajectories as well (since they will have to enter from all sides of the brain.) The failure of multiple catheters to cover such a non-spherical margin is a potential reason for failure of a trial with CED systems. As well, the low catheter infusion rate necessary to prevent unacceptable backflow significantly prolongs the period of treatment; and loss of infusate into the cavity itself occurs. Risk of bleeding and infection, as well as patient discomfort, are all increased.

Cavity Margin Infusion Device (CMID).

Figure 9:
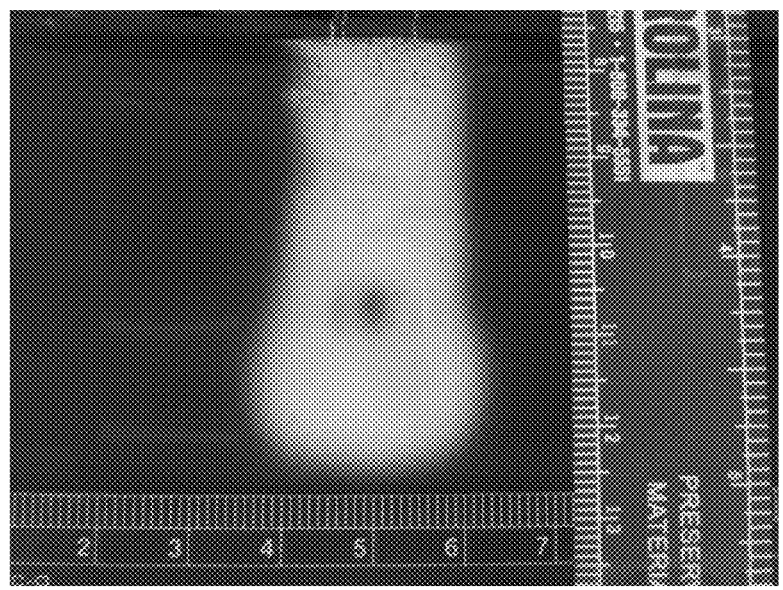
FIG. 9. The prototype of FIG. 7 is used with a pseudo-sulcus and a completely unsealed open cavity. The CMID effectively perfuses cavity margin in an open unsealed cavity even with pseudo-sulcus. This result is due to the myriad ports across which fluid may flow into the margins, radially out from the supporting surface of the balloon. This is in contrast with FIG. 4 where the fluid flow is tangential to the balloon and hence escapes to the surface of the gel (or, by analogy, to the cerebrospinal fluid in the sub-arachnoid space in a human or animal), and thereby failing to infuse into the margins of the cavity. Note that the infusion in this figure also does go to the top of the gel since there is no seal; however this does not compromise the successful infusion of the margins.
Figure 10:
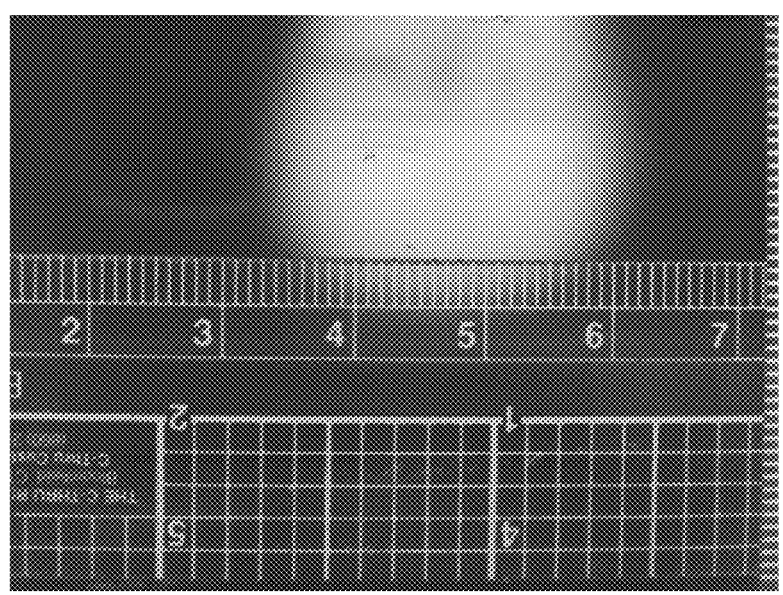
FIG. 10. A close up of the prototype of FIG. 9 is shown after some further infusion showing high concentration in the margins. The cavity in both cases is invisible since its visibility is blocked by the intervening dye.

We affixed hollow fiber catheters In a relatively symmetrical distribution) to a balloon surface to form a CMID that presses the catheters firmly against the cavity wall when the balloon is fully inflated. Dye infused through the catheters of this assembly effectively perfused the entire cavity margin. See FIGS. 9 and 10. Upon creating a pseudo-sulcus, the myriad fluid exit sites in the hollow fiber catheters on either side of the sulcus produced uniform tissue distribution of dye in the cavity margin, rather than loss into the low-resistance sulcus. Thus the CMID allows uniform dispersion of dye into the cavity margin, whether or not a pseudo-sulcus is present, and whether or not the cavity is sealed.

Technology questions addressed in this description include at least: (1) What is the best conformation of the balloon-catheter assembly? (2) How to achieve uniform infusate distribution in the 2 cm cavity margin? (3) How to achieve uniform agent delivery within a short time frame, and test if intraparenchymal pressure increases at high flow rates are benign. These issues are addressed (by way of example) in an in vitro phantom tissue gel model to create optimized Infusion Device usage parameters. The optimized devices in in vivo studies in porcine brain resection cavities and a scaled Infusion Device ex vivo in cow brain may be used to evaluate insertion methods and cavity sealing in a larger tissue platform using resection cavities appropriate for small to medium sized human tumors.

Construction and Validation of CMID in gel.

It seems that the CMID would be superior in performance to either of the CED alternatives, and this has been confirmed with even elementary prototypes in the gel studies. We may use a 0.2% Agarose gel for these studies. We are aware that 0.6% gel, sometimes at body temperature (37 Celsius) is more often used. However, it is significantly more brittle, quite unlike tissue, and its original justification is not necessarily relevant for studying distribution of fluid, and we have chosen the less brittle gel supporting higher flow rates.

Determination of preferred balloon designs for different cavity sizes/configurations.

Figure 5:
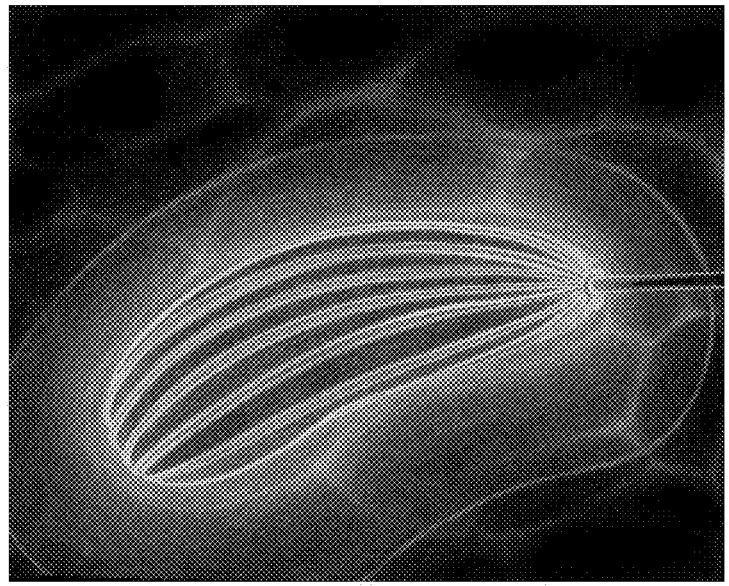
FIG. 5 illustrates a solution to both of the problems illustrated in FIGS. 3 and 4. An aspect of the problem solution is to have the entire surface of the inner wall of the margin (i.e., the wall circumscribing the cavity) be the source of infusion. One realization of this is to lay a number of porous membrane catheters along the meridians of the balloon, so that when inflated, these catheters lie snugly along the cavity walls and serve as sources of fluid.
Figure 11:
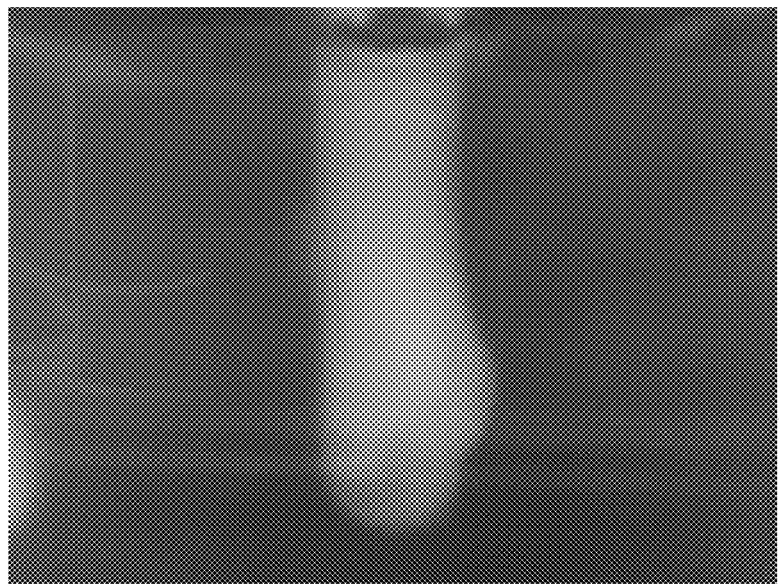
FIG. 11 shows a cavity with non-uniform shape. In this case a bulge shown by the shape adopted by dye introduced into the cavity can be addressed by compliant balloons which accommodate to the shape of the cavity as well as offer pressure against the walls of the cavity in ways that do not damage tissue.
Figure 12:
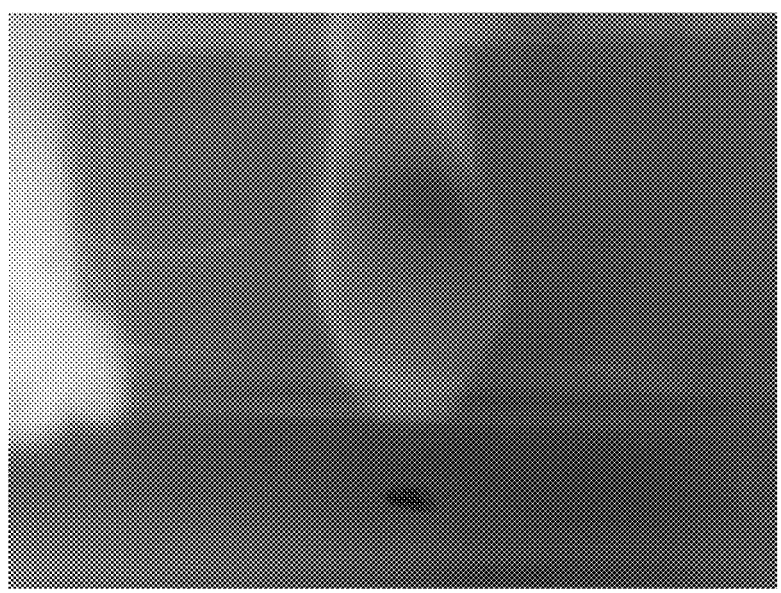
FIG. 12 also shows a cavity with non-uniform shape, in this case a bulge shown by the shape adopted by dye introduced into the cavity can be addressed by compliant balloons which accommodate to the shape of the cavity as well as offer pressure against the walls of the cavity in ways that do not damage tissue.

Tissue cavities created by tumor resection vary in size and shape, which cannot be adequately determined prior to surgery. While some resection cavities are ovoid, others may assume non-convex or other complicated shapes. We test 2 cm and 5 cm cavities as representative of large and small tumor removal, and for each diameter cavity we will construct 3 different internal shapes for testing with balloons of different compliances. Our goal is to determine the relevant variables of shape and compliance that affect a balloon's ability to conform to the walls of a non-uniform interior. See FIGS. 5, 11 and 12. Acquiring this information will allow us to scale balloons for use in other-sized cavities and shapes as found in clinical treatment.

Determine preferred catheter length and number for different cavity sizes and configurations—number of balloons and catheters TBD Having optimized some balloon configurations, the length of the catheters and the number of them to obtain the best coverage of margins in gels at a fixed flow rate that is not too high for a gel have also been examined. 4, 8, 9 and 12 catheters where the lengths are (a) sufficient to cover half a "great circle" distance on the inflated balloon, and then (b) only half again as long have been considered. "Length" here means the length of the porous membrane itself through which the efflux into the cavity or the margin occurs. We will use a flow rates from 5 to 20 μL/min per catheter for these tests. Such flow rates are not high for the gel, but unfortunately, gels in turn are not perfectly indicative of what is tolerable in tissue.

Determined allowable infusion rates in gel

The goal is to observe uniform dye distribution within a short time frame. We test high flow rates, up to 20 μL/min (such as from 5 to 1000 microliyters per minute), to determine at what infusion rates uniform dye distribution can be achieved and to learn whether there is loss of dye from the cavity entry site due to backflow or leak around the entry site gel seal. If high infusion rates through multiple balloon-supported microporous hollow fiber catheters (the CMID) provide uniform dye distribution with minimal leak or loss, this will allow substantial direct delivery of a therapeutic agent to the resection cavity margin in a limited number of hours following the surgical removal of tumor. The therapeutic treatment infusion can be completed while the patient is still in the operating room (e.g., within minutes of the excising surgery), and a subsequent surgery to remove the device at the completion of the infusion is avoided.

Construct collar around balloon to eliminate leak of glue to distal portions of balloon.

To eliminate leak of adhesive sealant into the resection cavity after it is applied the CMID-gel surface junction, we will first apply oxidized cellulose, Surgicel™ covering agent (Ethicon, Somerville N.J.), as "scaffolding" around the catheter proximal to the balloon portion, and then spray the scaffolding with the biocompatible adhesive sealant, DuraSeal™ covering agent (Covidien, Mansfield, Mass.) is a preparation of modified polyethylene glycol that when mixed with a solution of trilysine amine, rapidly forms a cross-linked biopolymer. This material is used clinically in neurosurgical applications, and would be acceptable for use for a similar purpose in human clinical applications.

Testing the Optimized Infusion Device configuration and infusion parameters.

The device will be tested in a 1.5 cm cavity created in 0.2% agarose gel. The CMID will be tested in its optimized configuration that presses the hollow fiber catheters firmly against the cavity wall. The balloon catheter's balloon will be inflated to achieve a spherical void 5 mm wide between the balloon and cavity wall into which the infused fluid will flow.

Fluid flow rates for the balloon catheter will vary between 5 and 15 μL/minute. Fluid flow rates for the CMID will be those determined in the prior experiments to yield the most uniform distribution and efficient transfer of dye. Tissue infusion pressures will be measured. For both devices, uniformity and volume of distribution of dye and time required for dye to reach 2 cm from the cavity margin will be assessed for each flow rate and pressure.

A sulcus-like defect in the cavity wall will serve as a test of the uniformity of dye distribution in the presence of a low pressure sink for both devices.

The uniformity and volume of dye distribution and the time required for dye to achieve flow throughout the 2 cm gel cavity margin will be assessed for each infusion method. Void loss and its effect upon dye distribution will be observed.

Determining the Efficacy of the CMID in Porcine Brain.

Testing the CMID configuration and infusion parameters.

The CMID configuration and infusion parameters will be tested in an in vivo porcine brain platform. The CMID will be tested in its optimized configuration, and will be scaled down to accommodate the smaller dimensions of the porcine brain.

Methods. In this section, we utilize the CMID design to demonstrate feasibility of rapid circumferential perfusion of the cavity margins with infusate.

The porcine brain has a mass less than one third that of a human brain, and the cerebral cortices and associated white matter are more reduced than the subcortical structures compared to human brain. For this reason, we have designed the studies to incorporate a 5 mm diameter surgical cavity extending 15 mm into the porcine brain. This will allow monitoring of infusate distribution within the parenchyma to 5 to 10 mm from the cavity margin before encountering adjacent surface structures, such as ventricle or cortical sulcus. Four pigs will be used, and a resection cavity created in each hemisphere. The CMID will be placed in each resection cavity.

Animals will be prepared by induction, intubation and inhalational anesthesia in the University of Virginia Imaging Research Center with the assistance of staff. Under aseptic conditions a midline scalp incision will be carried down to bone and the pericranium will be elevated and the scalp retracted bilaterally. Bun holes (12 mm in diameter) will then be placed on each side of midline, centered 16 mm lateral to midline and 16 mm anterior to lambda (the junction of the sagittal and lambdoidal sutures). The dura will be opened, and then Navigus™ stereotactic guides (Medtronic, Minneapolis, Minn.) (2 total) will be fixed in place centered over each burr hole. Gadolinium-containing inserts will be placed into each trajectory guide, and the guides will be adjusted to have angles 20 degrees medial and 15 degrees posterior from vertical. The animals will be transferred to the MR scanner and images obtained to confirm the proper trajectories set with the Navigus guides. If necessary, trajectory adjustments will be made and confirmed by scan. Having confirmed the proper trajectories, the cavities will be formed by slowly advancing a 5 mm twist drill to the proper depth in the brain. After forming the cavity, the Navigus™ guide will be removed, and the cavity will be debrided and hemostasis will be accomplished by standard neurosurgical technique. The cavity diameter will be evaluated and adjusted using surgical instruments calibrated with a 5 mm diameter. The technique described for creating a defect in the living porcine brain will ensure a relatively uniform cavity size and placement. While the surgical cavities could have neurologic consequences for the subject animals, the studies proposed are not survival studies, so that any neurologic consequences of the bilateral brain cavities will not be experienced by the animals.

After forming the bilateral surgical cavities, the CMID device will be advanced into the proper depth as determined by simple experimentation. Viewing the pathway flow of infusate from the CMID will give simple, viewable data on ranges of appropriate placement of the device
Gadoteridol infusion to assess uniformity of tracer distribution Following placement of the infusion devices bilaterally, infusions of gadoteridol (Prohance™ brand infusate) will be carried out using infusion parameters determined primarily by results of infusion testing to be carried out in brain surrogate gel material. Two sets of parameters will be tested with the CMID, with 3 to 4 replicates for each of the parameters. Animals will be studied individually sequentially to allow modifications of the infusion procedure based on analysis of data from previous animal studies. Distribution analysis will be performed as described elsewhere.
Measurement of tissue interstitial pressure during infusion Tissue interstitial pressures to ascertain pressures under the high flow rates planned are measured. We will use a commercially available MR-compatible fiber optic pressure sensor (Fiso Technologies, Quebec, Canada). The sensor catheter will be manufactured to have properties comparable to other ICP monitoring catheters and will be inserted under MR guidance to reach a parenchymal location 5 mm from the cavity wall, where it will be secured.

In summary, the studies involve two infusion parameters and corresponding pressure measurements to be performed with the CMID, for a total of 4 animals. These observations will provide up to four animals infused with the CMID for each infusion condition. The resulting data is expected to provide evidence for the feasibility and reliability of the CMID for infusing cavity margins in living brain. Between the results in gels and these results in living brain, significant understanding of the operating range of infusion parameters should be acquired.

MR Distribution Analysis MR scanning sequences used to acquire images (pre-infusion and during infusion) will be performed with the contrast agent, Prohance™ infusate, at 2 mM concentration. The animal will be in the scanner throughout the infusion procedure. Prior to infusion we will take baseline scans to plan catheter placement. We will then use high resolution Fast Spoiled Gradient-Recalled Echo (FSPGR) imaging to allow us to delineate the cavity by hand for subsequent masking. (The cavity cannot be adequately masked by simple thresholding of the image.) The concentration of the contrast agent will be measured by techniques traditionally used in the field. The scan sequences used may include dual flip-angle T1, and actual flip angle imaging (AFI). Subsequently, the higher resolution FSPGR's may be interleaved with the concentration mapping sequences, and with the improved imaging quality of these interleaved images, we can visualize tracer in tissue after masking out the cavity with higher resolution than with the concentration mapping, albeit without quantification. In addition to these measurements desirable in performing these methods, it is also possible to obtain Fluid Attenuated Inversion Recovery (FLAIR) sequences which may serve to mask the CSF (cerebrospinal fluid, usually as a leak). This assists in analyzing how much tracer remains in tissue during the infusion process. It is to be noted that the cavity in the practice of our technology may be relatively filled (e.g., 60%, 70%, 80%, 85%, 90%, even 95% of cavity volume) by the balloon rather than by fluids (such as water or aqueous solutions), gases (usually inert gases). Furthermore the FLAIR is lower resolution than the FSPGR images. Hence we may use the latter to remove the cavity from a distribution assessment.

It is possible to use acoustic shepherding of the infusate to amplify benefits of the present technology. Sonic waves, under controlled guidance of an operator using processor controls, can direct, restrict, or enhance the directional flow or retention or positioning of the infusate. To assist in the enabling of that embodiment, U.S. patent application Ser. No. 12/319,311, filed 6 Jan. 2009, is incorporated herein by reference in its entirety.

The imaging described herein will evaluate the uniformity, concentration, and volume of tracer distribution, and the ability of tracer to achieve flow throughout the 2-15 mm, or 5 to 10 mm (diameter) brain cavity margin. Void loss and its effect on tracer distribution will be observed. We expect the CMID will deliver a greater and more uniform volume of distribution of tracer than may be expected with balloon catheter or multi-needle CED infusions, although direct comparison with these infusion methods will await Phase II of the project. We also expect the time to achieve flow to the 2 cm margin will be significantly shorter for the CMID. We anticipate that, at any flow rate, the CMID will lose less fluid into a tissue void or sulcus than is observed with balloon catheter or multi-needle CED infusions.
Histological Evaluation of tissue following infusion At the conclusion of the examples, animals can be euthanized, and representative brain samples submitted for pathologic analysis with hematoxylin and eosin stain. Tissue can be examined for evidence of cellular distortion, early signs of inflammation, and fluid or blood distribution in non-standard patterns.

Demonstrating the Use of the Scaled CMID in Cow Brain

The bovine brain is approximately 30% smaller in dimensions than the human brain, and this will enables study of cavity margin infusions on the order of small cavities in humans. The range of experience acquired with each off the test platforms is also expected to allow assessment the further scalability to larger human tumor cavities. Insertion methods and infusion parameters for a scaled Infusion Device will be evaluated in 1.5 cm resection cavities in 4 ex vivo bovine brains to develop the techniques required to treat small to medium-sized human tumors. Methods of device insertion can be evaluated to determine the best technical methods to deploy the CMIC in the first 2 bovine brains. In the second 2 bovine brains, the uniformity and volume of tracer distribution following Device insertion will be assessed by MRI. Void loss and its effect upon tracer distribution will be observed. Evidence of exit site leak will be evaluated by visual inspection and MRI image evaluation.

Methods. Fresh bovine brains are first subjected to baseline MR imaging to obtain assessments of their dimensions and anatomy. Prior to imaging, fiducial markers (commercial vitamin E capsules) will be embedded in the surface of each hemisphere for localization and relationship of surface structures to deeper anatomy. Following this imaging, trajectories can be planned and trial catheters (Ventricular Catheter, Medtronic, Goleta, Calif.) will be placed. The brains will then be re-imaged in order to confirm the adequacy of the trajectories established. Corticectomies can then be performed at the catheter sites, and brain parenchyma will be removed from around the catheters to the full extent of the trajectories to produce 1.5 cm diameter cavities. Surgical instruments with calibrated diameters will be used to insure that the cavities established are equal in size in both hemispheres, and consistently formed. Following completion of the cavity formation, CMIDs will be placed in both cavities.

Gadoteridol infusion to assess uniformity of tracer distribution

Infusions will then be carried out in a fashion similar to that described above. As further noted above, covering and sealing of the entrance of the CMIDs into their respective cavities may require use of Surgicel™ scaffolding covered by DuraSeal. Infusion parameters for these studies will be determined by the results of the infusion studies described or performed above. Distribution analysis will be performed as described herein.

MR Distribution Analysis

The scanning sequences and analyses for this aspect will be identical to those described above for analysis of tracer distribution observed in porcine brain.

Successful deployment and infusion with the CMID in pig and cow brains will warrant submission of a Phase II SBIR proposal culminating in FDA approval and use in human patients.

Potential Pitfalls and Alternative Approaches.

Catheters do not remain uniformly distributed around cavity wall when device inserted into cavity.

Alternative Approaches.

Within the scope of the present technology, it is possible to develop different methods to array catheters around balloon surface, as by forming a helix of multiple catheters, or a single catheter more tightly wound over the surface of the balloon. It is further possible to revise catheter fastening and restraining configuration at opposite poles of the balloon. Expandable spacers (e.g., inflatable tubes) between catheters can be used, or the individual or collective catheters may be adjusted by embedded guidewires or thermally responsive or electrically responsive (expandable or contractable, e.g., by electrical rearrangement or thermal expansion or shrinkage) components or coverings on the balloon may be used to position or reposition catheters.

Any non-invasive imaging (or even optical fiber images) such as MR imaging may be used to assess whether flow from catheters is emanating from the full length of the catheter. If flow is limited to a portion of the catheter, the system should be examined to determine whether pores are occluded by foreign matter, such as gel or tissue. It is desirable to determine whether maintaining specific catheter flow levels during device cavity insertion will prevent pore occlusion. Sensing to evaluate tissue pressure to determine whether there is a relevant impedance mismatch is also possible.

Evaluation of performance of this technology, and planning specific applications may include assessing whether restricted axial flow is occurring (due to structural factors, flow rates, liquid viscosity and the like and if deployed catheter geometry (a bend or kink) or partial occlusion is present. Sensors may be provided in the device to assess at least some of these factors by transmitting the sensed information to a processor. If catheter geometry is at fault, planning with an interventional method would be desirable to retain functional catheter geometry during insertion. If axial flow is restricted, there should be a method for examining or determining whether infusion channel is obstructed by gel or tissue.

If there is a potential problem with an Infusate leak from cavity entry site, there can be an alternative approach. There may be sensors or visual observation capability to test the use of biodegradable sealant to seal cavity entry site, after the infusion device is inserted, to prevent leak.

Objectives of this technology in uniformity and volume of distribution of dye and tracer will be achieved. It is believed that an effective infusion rate will be greater with CMID than effective rates for balloon catheter or multi-needle CED infusions of the prior art. Loss of dye into low pressure sinks will be less with CMID than effective rates for balloon catheter or multi-catheter CED infusions.

The above descriptions are provided to enable practice of a generic invention relating to mrthods, systems and apparatus. Those descriptions, even though using specific materials, dimensions, rates, and parameters, are merely illustrative species and are not intended to limit the scope of the invention claimed.

What is claimed:

1. A method of providing medically active liquid to tissue surrounding a surgically-created cavity, the method comprising:
    positioning a liquid-delivery device within the cavity;
        the delivery device having an exterior surface, the delivery device having length, width and depth, and multiple openings in the exterior surface distributed throughout the length and width of the delivery device;
    adjusting dimensions of the exterior surface of the liquid delivery device to better fill inside dimensions of the cavity;
    delivering the medically active liquid to the tissue surrounding the surgically-created cavity through the multiple openings;
    moving the medically active liquid out of the multiple openings at a delivery rate through the multiple openings:,
    wherein the fluid resistance of the openings for a given area of the surface of the delivery device is matched to a corresponding fluid resistance of the tissue over the same area as that of the multiple openings to ensure uniformity of the delivery through the openings.

2. The method of claim 1 wherein the medically active liquid is moved out of the multiple openings at a delivery rate through the multiple openings such that the delivery rate through a single one of the multiple openings does not vary by more than 20% from a numerical rate average for all of the multiple openings.

3. The method of claim 1 wherein the exterior delivery device is a flexible expandable component and the dimensions on the flexible expandable component are adjusted by hydraulic or pneumatic pressure.

4. The method of claim 3 wherein the fluid resistance of the multiple openings is designed to be greater than that of the tissue over the same surface area as the multiple openings to ensure uniformity of delivery through the openings.

5. The method of claim 4 wherein the inflatable component shapes the interior walls of a tissue margin by pressure from the expandable component.

6. The method of claim 4 wherein the inflatable component is shaped by application of pressure within the flexible expandable component to conform the surface of the inflatable element to interior wall of a tissue margin after surgical creation of a reaction cavity.

7. The method of claim 4 wherein the medically active liquid is delivered into liquid delivery catheters at the multiple openings at equal pressure.

8. The method of claim 7 wherein the medically active liquid is delivered into each liquid delivery catheter at an individually controlled pressure for each liquid delivery catheter.

9. The method of claim 4 wherein the medically active liquid is delivered into liquid delivery catheters at the multiple openings at an individually controlled pressure for each liquid delivery catheter.

10. The method of claim 3 wherein there are liquid-delivery catheters distributed over the surface of the inflatable component and at least some of the liquid-delivery catheters comprise a) porous membranes or b) closed tubes with multiple openings formed in walls of the tube.

11. The method of claim 10 wherein medically active liquid is moved through the multiple openings and into the cavity within 2 hours of excision of tissue.

12. The method of claim 1 wherein the delivery device comprises a flexible and inflatable component having a surface and a volume, with the multiple openings distributed in three dimensions over the surface of the inflatable component.

13. The method of claim 1 wherein the inflatable component comprises an inner flexible balloon and an outer flexible balloon, the outer flexible balloon having the multiple openings therein, the method further comprising providing the medically active liquid into a volume between the inner flexible balloon and the outer flexible balloon.

14. The method of claim 1 wherein the multiple openings distributed in three dimensions over the surface of a volume of the inflatable component comprise at least eight flexible liquid delivery catheters distributed over the surface of the inflatable component, each liquid delivery catheter having multiple ones of the multiple openings along lengths of the liquid delivery catheters, and the medically active liquid is delivered from the liquid delivery catheters through the multiple ones of the multiple openings along lengths of the liquid delivery catheters.

15. The method of claim 1 wherein the fluid resistance of the multiple openings for a given area of the surface of the delivery device is matched to a fluid resistance of the tissue over the same area as the multiple openings to ensure uniformity of the delivery through the openings.

16. The method of claim 1 wherein the fluid resistance of the multiple openings is designed to be greater than that of the tissue over the same surface area of the multiple openings to ensure uniformity of delivery through the openings.

17. The method of claim 1 wherein there are liquid-delivery catheters distributed over the surface of the inflatable component and at least some of the liquid-delivery catheters comprise a) porous membranes or b) closed tubes with multiple openings formed in walls of the tube.

18. A method of providing medically active liquid to tissue surrounding a surgically-created cavity, the method comprising:
    positioning a liquid-delivery device within the cavity;
        the delivery device having an exterior surface, the delivery device having length, width and depth, and multiple openings in the exterior surface distributed throughout the length and width of the delivery device;
        adjusting dimensions of the exterior surface of the liquid delivery device to better fill inside dimensions of the cavity;
        delivering the medically active liquid to the tissue surrounding the surgically-created cavity through the multiple openings;
        moving the medically active liquid out of the multiple openings at a delivery rate through the multiple openings;
    wherein the fluid resistance of the openings for a given area of the surface of the delivery device is matched to a corresponding fluid resistance of the tissue over the same area as that of the multiple openings to ensure uniformity of the delivery through the openings;
    wherein the multiple openings distributed in three dimensions over the surface of a volume of the inflatable component comprise at least four liquid-delivery catheters distributed over the surface of the inflatable component, each liquid delivery catheter having multiple ones of the multiple openings along lengths of the liquid delivery catheters, and the medically active liquid is delivered from the liquid delivery catheters through the multiple ones of the multiple openings along lengths of the liquid delivery catheters.

19. The method of claim 18 wherein pneumatic pressure is imposed in the medically active liquid within the volume of the inflatable component between an inner flexible balloon and an outer flexible balloon which form the inflatable component, forcing the medically active liquid to pass through the multiple openings in the outer flexible balloon.

20. A method of providing medically active liquid to tissue surrounding a surgically-created cavity, the method comprising:
    positioning a liquid-delivery device within the cavity;
        the delivery device having an exterior surface, the delivery device having length, width and depth, and multiple openings in the exterior surface distributed throughout the length and width of the delivery device;
        adjusting dimensions of the exterior surface of the liquid delivery device to better fill inside dimensions of the cavity;
        delivering the medically active liquid to the tissue surrounding the surgically-created cavity through the multiple openings;
        moving the medically active liquid out of the multiple openings at a delivery rate through the multiple openings:,
    wherein the fluid resistance of the openings for a given area of the surface of the delivery device is matched to a corresponding fluid resistance of the tissue over the same area as that of the multiple openings to ensure uniformity of the delivery through the openings;
    wherein the multiple openings distributed in three dimensions over the surface of a volume of the inflatable component comprise at least sixteen liquid-delivery catheters distributed over the surface of the inflatable component, each liquid delivery catheter being a narrow tube with a distal opening, or an end port catheter, these catheters being of different lengths so that at least 16 openings are distributed over the surface of the inflatable component, and the medically active liquid is delivered from the liquid delivery catheters through the multiple openings at ends of the liquid delivery catheters.

* * * * *